United States Patent
Frey et al.

(10) Patent No.: US 11,769,073 B2
(45) Date of Patent: Sep. 26, 2023

(54) METHODS AND SYSTEMS FOR PRODUCING AN EXPANDED TRAINING SET FOR MACHINE LEARNING USING BIOLOGICAL SEQUENCES

(71) Applicant: Deep Genomics Incorporated, Toronto (CA)

(72) Inventors: Brendan John Frey, Toronto (CA); Andrew Thomas DeLong, Toronto (CA); Hui Yuan Xiong, Toronto (CA)

(73) Assignee: DEEP GENOMICS INCORPORATED, Toronto (CA)

(*) Notice: Subject to any disclaimer, the term of this patent is extended or adjusted under 35 U.S.C. 154(b) by 1216 days.

(21) Appl. No.: 16/179,280

(22) Filed: Nov. 2, 2018

(65) Prior Publication Data
US 2019/0073443 A1    Mar. 7, 2019

Related U.S. Application Data (63) Continuation of application No. PCT/CA2016/050510, filed on May 4, 2016.

(51) Int. Cl.
| | | |
|---|---|---|
| G01N 33/48 | (2006.01) | |
| G01N 33/50 | (2006.01) | |
| G06N 20/00 | (2019.01) | |
| G16B 30/00 | (2019.01) | |
| G16B 40/00 | (2019.01) | |
| G16B 40/20 | (2019.01) | |
| G16B 40/30 | (2019.01) | |
| G06F 18/2411 | (2023.01) | |
| G06N 3/047 | (2023.01) | |
| G16B 5/00 | (2019.01) | |
| G06N 3/088 | (2023.01) | |
| G06N 7/00 | (2023.01) | |

(52) U.S. Cl.
CPC ......... *G06N 20/00* (2019.01); *G06F 18/2411* (2023.01); *G06N 3/047* (2023.01); *G06N 3/088* (2013.01); *G06N 7/00* (2013.01); *G16B 5/00* (2019.02); *G16B 30/00* (2019.02); *G16B 40/00* (2019.02); *G16B 40/20* (2019.02); *G16B 40/30* (2019.02)

(58) Field of Classification Search
CPC .......... G16B 40/20; G16B 5/00; G16B 30/00; G16B 40/00; G16B 40/30; G06K 9/6269; G06N 3/0472; G06N 3/088; G06N 7/00; G06N 20/00

See application file for complete search history.

(56) References Cited

U.S. PATENT DOCUMENTS

| | | |
|---|---|---|
| 2005/0084907 A1 | 4/2005 | Fox |
| 2008/0300797 A1 | 12/2008 | Tabibiazar et al. |
| 2014/0214391 A1 | 7/2014 | Cope |

FOREIGN PATENT DOCUMENTS

WO    WO-2017190211 A1    11/2017

OTHER PUBLICATIONS

Bernardes et al. A review of protein function prediction under machine learning perspective. Recent Patents on Biotechnology, vol. 7, pp. 122-141. (Year: 2013).*
Cristofaro et al. Mutations in the ribonuclease H active site of HIV-RT reveal a role for this site in stabilizing enzyme-primer-template binding. Biochemistry, vol. 41, pp. 10968-10975. (Year: 2002).*
International search report dated Dec. 22, 2016 for PCT Application No. PCT/CA2016/050510.
EP16900781.2 The Extended European Search Report dated Nov. 28, 2019.
Kim, et al. Probabilistic Models for Semisupervised Discriminative Motif Discovery in DNA Sequences. IEEE/ACM Transactions on Computational Biology and Bioinformatics, vol. 8, No. 5, pp. 1309-1317, Sep.-Oct. 2011.
Nonnemaker, Jean E. The safe use of synthetic data in classification. Lehigh University, 2008. Nonnemaker.
Pajapakse, et al. Markov encoding for detecting signals in genomic sequences. IEEE/ACM Transactions on Computational Biology and Bioinformatics 2.2 (2005): 131-142.
Simonyan, et al. Deep inside convolutional networks: Visualising image classification models and saliency maps.arXiv preprint arXiv:1312.6034 (2013).
Exam Report issued in Canadian Patent Application No. 3,022,907 dated May 11, 2022.

* cited by examiner

*Primary Examiner* — Russell S Negin
(74) *Attorney, Agent, or Firm* — Wilson Sonsini Goodrich & Rosati (57) ABSTRACT

Methods and systems for expanding a training set of one or more original biological sequences are provided. An original training set is obtained, wherein the original training set comprises one or more original biological sequences. Saliency values corresponding to one or more elements in each of the one or more original biological sequences are obtained. For each of the original biological sequences, one or more modified biological sequences are produced and the one or more modified biological sequences are associated with the original biological sequence. One or more elements are generated in each of the one or more modified biological sequences using one or more elements in the associated original biological sequence and the corresponding saliency values. The one or more modified biological sequences for each of the original biological sequences are added to the original training set to form an expanded training set.

18 Claims, 11 Drawing Sheets

METHODS AND SYSTEMS FOR PRODUCING AN EXPANDED TRAINING SET FOR MACHINE LEARNING USING BIOLOGICAL SEQUENCES

CROSS-REFERENCE

This application is a Continuation Application of International Patent Application No. PCT/CA2016/050510, filed May 4, 2016, which is hereby incorporated by reference in its entirety.

TECHNICAL FIELD

The following relates generally to machine learning and, more particularly to methods and systems for producing an expanded training set for machine learning using biological sequences.

BACKGROUND

Precision medicine, genetic testing, therapeutic development, patient stratification, health risk assessment, proactive health planning, and patient networks are increasingly making use of machine learning models that are trained using biological sequence data, which may include DNA, RNA and protein sequences.

Supervised learning may be used to train a machine learning model to take a biological sequence as input and to output a label, a set of labels or more structured information that is associated with the input sequence. The labels may correspond to molecular phenotypes. Examples include predicting chromatin state from DNA sequence, predicting splice sites from DNA sequence, predicting polyadenylation sites from RNA sequence, predicting protein stability from protein sequence, predicting protein-protein interactions from protein sequences, and predicting protein-DNA interactions from protein and DNA sequences. The associated label, set of labels or more structured information may be determined from a discrete molecular phenotype or a continuous molecular phenotype, such as the percent of transcripts with an exon spliced in, a gene expression level, or the concentration of a protein complex, or it may be determined by some other means, such as by labeling sequences as pathogenic or non-pathogenic using clinical data.

Machine learning models that are commonly used for supervised learning in the context of biological sequences include linear regression, logistic regression, neural networks, convolutional networks, deep neural networks, recurrent neural networks, long short-term memory networks, Gaussian processes, decision trees, random forests and support vector machines. While there are many supervised learning models, they all have in common that, for training, they require a training set consisting of biological sequences and associated labels. In some cases, the input may be multiple biological sequences, such as in the case of predicting protein-DNA interactions, where the input may be a protein sequence and a DNA sequence.

Unsupervised learning may be used to train a machine learning model to take a biological sequence as input and output a set of features that are useful in describing the input. This is called feature extraction. One of the features may be a real number that scores the sequence, using log-likelihood or squared error. Extracted features may be used for visualization, for classification, for subsequent supervised learning, and more generally for representing the input for subsequent storage or analysis. In some cases, each training case may consist of multiple biological sequences. Examples include extracting features from DNA promoter sequences, extracting features from RNA splice sites, extracting features from pairs of DNA sequences that are in chromatin contact, and extracting features from pairs of protein sequences that are in contact.

Machine learning models that are commonly used for unsupervised learning in the context of biological sequences include k-means clustering, mixtures of multinomial distributions, affinity propagation, discrete factor analysis, hidden Markov models, Boltzmann machines, restricted Boltzmann machines, autoencoders, convolutional autoencoders, recurrent neural network autoencoders, and long short-term memory autoencoders. While there are many unsupervised learning models, they all have in common that, for training, they require a training set consisting of biological sequences, without associated labels.

Over-fitting is a recognized problem in both supervised and unsupervised machine learning. This is a situation where a model effectively memorizes the training data and will therefore fail to generalize well to new examples. One solution is to obtain more training data, but this may not be possible, especially in biology, where new data often require expensive and time consuming laboratory studies. Herein we describe an approach to generating additional biological sequences by modifying original biological sequences in a way that does not substantially alter their biological functions.

SUMMARY

In one aspect, a method for producing an expanded training set for machine learning using biological sequences is provided, comprising obtaining an original training set, wherein the original training set comprises one or more original biological sequences, obtaining saliency values corresponding to one or more elements in each of the one or more original biological sequences, for each of the original biological sequences, producing one or more modified biological sequences and associating the one or more modified biological sequences with the original biological sequence, generating one or more elements in each of the one or more modified biological sequences using one or more elements in the associated original biological sequence and the corresponding saliency values, and adding the one or more modified biological sequences for each of the original biological sequences to the original training set to form an expanded training set.

The probability that an element in each of the one or more modified biological sequences is the same as the element in the associated original biological sequence can be higher for larger corresponding saliency values.

Each of the one or more original biological sequences can have an associated label, and each of the one or more modified biological sequences can be associated with the same label as the associated original biological sequence.

The machine learning can comprise one of: a mixture model, a hidden Markov model, an autoencoder, a recurrent neural network, linear regression, a neural network, a random forest, and a support vector machine.

The generating one or more elements in each of the one or more modified biological sequences using one or more elements in the associated original biological sequence and the corresponding saliency values can comprise determining a set of generator parameters from one or more elements in the associated original biological sequence and the corresponding saliency values, and using the set of generator parameters to generate the one or more elements in each of the one or more modified biological sequences.

At least one of the original biological sequences can be a DNA, RNA or protein sequence.

The generating of one or more elements in each of the one or more modified biological sequences can comprise producing a null symbol, which represents a deleted element in the modified biological sequence.

The saliency values can be derived from one or more of: evolutionary conservation across at least two different species, allele frequency in a human population, DNA accessibility, ChIP-Seq, CLIP-Seq, SELEX, massively parallel reporter assays, and mutational studies.

The probability of generating a value $\alpha$ for element $\hat{x}_i$ in one or more elements in each of the one or more modified biological sequences can be:

$$h(s_i)I(\alpha,x_i)+(1-h(s_i))/\hat{k}_i$$

where $x_i$ is the element in the original biological sequence, $s_i$ is the saliency value, $\hat{k}_i$ is the number of possible values for $\hat{x}_i$, $I(\cdot)$ is the indicator operator which outputs 1 if $\alpha=x_i$ and outputs 0 otherwise, and $h(s_i)$ is a linear or non-linear function of $s_i$.

The probability of generating a value $\alpha$ for element $\hat{x}_i$ in one or more elements in each of the one or more modified biological sequences can be:

$$h(s_i)I(\alpha,x_i)+(1-h(s_i))s_{i,\alpha}'$$

where $x_i$ is the element in the original biological sequence, $s_i$ is the saliency value, $\hat{k}_i$ is the number of possible values for $\hat{x}_i$, $I(\cdot)$ is the indicator operator which outputs 1 if $\alpha=x_i$ and outputs 0 otherwise, $h(s_i)$ is a linear or non-linear function of $s_i$, and $s_{i,\alpha}'$ is a non-uniform distribution over $\alpha \in \hat{A}_i$ satisfying $s_{i,\alpha}' \geq 0$, $\forall \alpha \in \hat{A}_i$ and $\Sigma_{\alpha \in \hat{A}_i} s_{i,\alpha}'=1$, where $\hat{A}_i$ is the set of possible values for $\hat{x}_i$.

In another aspect, a system for producing an expanded training set for machine learning using biological sequences is provided, the system comprising one or more computers and one or more storage devices storing instructions that, when executed by the one or more computers, cause the one or more computers to perform operations comprising: obtaining an original training set, wherein the original training set comprises one or more original biological sequences, obtaining saliency values corresponding to one or more elements in each of the one or more original biological sequences, for each of the original biological sequences, producing one or more modified biological sequences and associating the one or more modified biological sequences with the original biological sequence, generating one or more elements in each of the one or more modified biological sequences using one or more elements in the associated original biological sequence and the corresponding saliency values, and adding the one or more modified biological sequences for each of the original biological sequences to the original training set to form an expanded training set.

The probability that an element in each of the one or more modified biological sequences is the same as the element in the associated original biological sequence can be higher for larger corresponding saliency values.

Each of the one or more original biological sequences can have an associated label, and each of the one or more modified biological sequences can be associated with the same label as the associated original biological sequence.

The machine learning can comprise one of: a mixture model, a hidden Markov model, an autoencoder, a recurrent neural network, linear regression, a neural network, a random forest, and a support vector machine.

The generating one or more elements in each of the one or more modified biological sequences using one or more elements in the associated original biological sequence and the corresponding saliency values can comprise determining a set of generator parameters from one or more elements in the associated original biological sequence and the corresponding saliency values, and using the set of generator parameters to generate the one or more elements in each of the one or more modified biological sequences.

At least one of the original biological sequences can be a DNA, RNA or protein sequence.

The generating of one or more elements in each of the one or more modified biological sequences can comprise producing a null symbol, which represents a deleted element in the modified biological sequence.

The saliency values can be derived from one or more of: evolutionary conservation across at least two different species, allele frequency in a human population, DNA accessibility, ChIP-Seq, CLIP-Seq, SELEX, massively parallel reporter assays, and mutational studies.

The probability of generating a value $\alpha$ for element $\hat{x}_i$ in one or more elements in each of the one or more modified biological sequences can be:

$$h(s_i)I(\alpha,x_i)+(1-h(s_i))/\hat{k}_i$$

where $x_i$ is the element in the original biological sequence, $s_i$ is the saliency value, $\hat{k}_i$ is the number of possible values for $\hat{x}_i$, $I(\cdot)$ is the indicator operator which outputs 1 if $\alpha=x_i$ and outputs 0 otherwise, and $h(s_i)$ is a linear or non-linear function of $s_i$.

The probability of generating a value $\alpha$ for element $\hat{x}_i$ in one or more elements in each of the one or more modified biological sequences can be:

$$h(s_i)I(\alpha,x_i)+(1-h(s_i))s_{i,\alpha}'$$

where $x_i$ is the element in the original biological sequence, $s_i$ is the saliency value, $\hat{k}_i$ is the number of possible values for $\hat{x}_i$, $I(\cdot)$ is the indicator operator which outputs 1 if $\alpha=x_i$ and outputs 0 otherwise, $h(s_i)$ is a linear or non-linear function of $s_i$, and $s_{i,\alpha}'$ is a non-uniform distribution over $\alpha \in \hat{A}_i$ satisfying $s_{i,\alpha}' \geq 0$, $\forall \alpha \in \hat{A}_i$ and $\Sigma_{\alpha \in \hat{A}_i} s_{i,\alpha}'=1$, where $\hat{A}_i$ is the set of possible values for $\hat{x}_i$.

These and other aspects are contemplated and described herein. It will be appreciated that the foregoing summary sets out representative aspects of methods and systems for producing an expanded training set for machine learning using biological sequences to assist skilled readers in understanding the following detailed description.

DESCRIPTION OF THE DRAWINGS

The features of the invention will become more apparent in the following detailed description in which reference is made to the appended drawings wherein.

DETAILED DESCRIPTION

For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

The biological function of a DNA, an RNA or a protein sequence is often invariant to certain modifications of the sequence, and this invariance can be used to generate new training sequences from an original set of training sequences.

For instance, consider an exon that is efficiently spliced into transcripts in human cells. Consider further the DNA sequence that starts 20 nucleotides upstream of the 3' splice site of the exon and ends 10 nucleotides downstream of the same splice site. If the same splice site in a wide range of mammals is located and the conservation of each of the 30 nucleotides across the mammals is examined, nucleotides can be identified that are highly conserved and nucleotides can be identified that are not conserved, that is, that vary across mammals. The highly conserved nucleotides are more likely to be functional, whereas the unconserved nucleotides are less likely to be functional. If we were to mutate an unconserved nucleotide, it is likely that when the spliceosome is processing the primary RNA sequence, the exon will still be efficiently spliced. That is, splicing of the exon by the spliceosome is invariant to the mutation. On the other hand, if we were to mutate a highly conserved nucleotide, it is substantially less likely that the spliceosome will efficiently splice the exon into transcripts; some transcripts may not include the exon. That is, splicing of the exon by the spliceosome is not invariant to the mutation. Given an original training set of sequences and corresponding labels for whether or not splicing occurs, we can expand the training set by modifying the nucleotides that are least conserved.

As another example, consider a protein binding domain from a protein in human cells and consider an amino acid sequence extracted from the binding domain plus 5 amino acids on either end. Suppose we have training cases consisting of such protein sequences along with corresponding labels for the binding affinity of each protein. If we examine the conservation of the amino acids, this time at the protein level, we can identify amino acids that are least conserved and expand the training set by modifying those amino acids appropriately.

The system and method described herein take as input a training set of original biological sequences and a corresponding set of saliency maps that indicate the degree to which each sequence element is important for biological function, and output a set of modified sequences. These modified sequences may be added to the training set to obtain an expanded training set.

Figure 1:
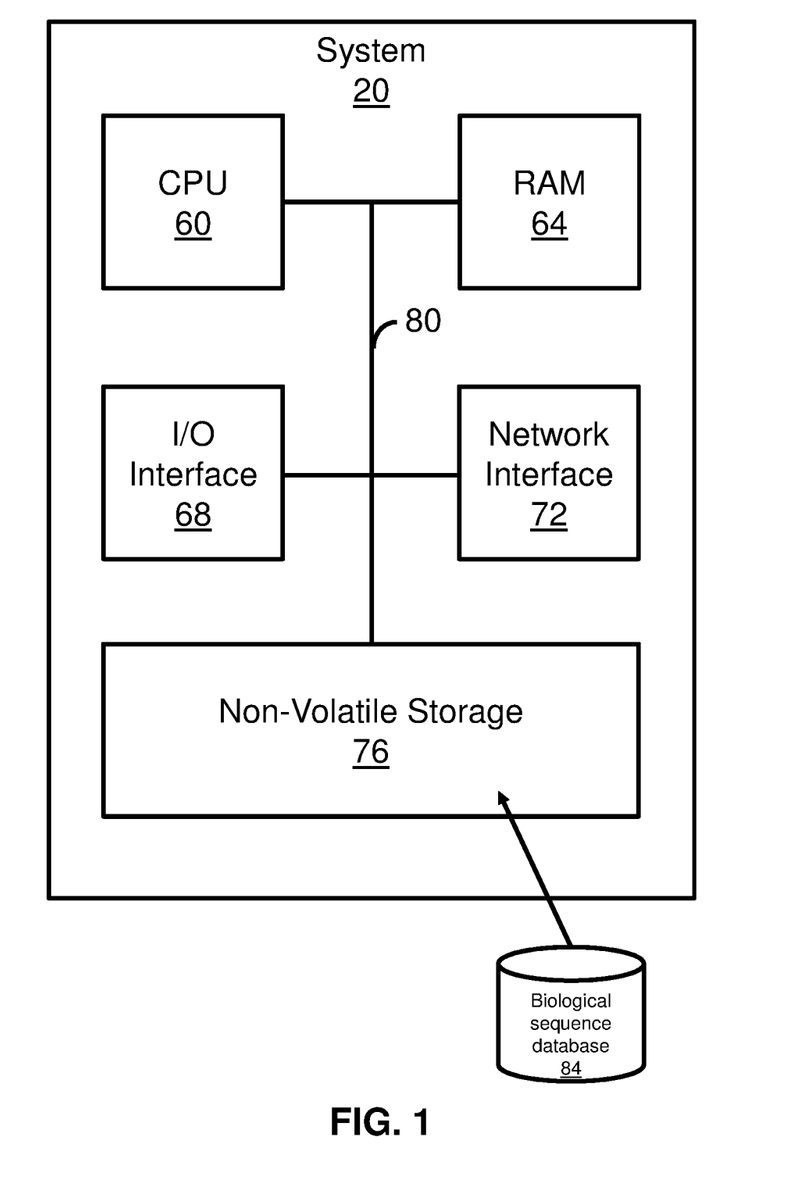
FIG. 1 is a system for generating biological sequences for training machine learning models in accordance with an embodiment.

FIG. 1 shows various physical components of a system 20 for generating training data for use in supervised and unsupervised learning from biological sequences. As will be appreciated, while the system 20 is illustrated as being a single physical computer, it can alternatively be two or more computers acting cooperatively to provide the functionality described. As shown, the system 20 has a number of physical and logical components, including a central processing unit ("CPU") 60, random access memory ("RAM") 64, an input/output ("I/O") interface 68, a network interface 72, non-volatile storage 76, and a local bus 80 enabling the CPU 60 to communicate with the other components. The CPU 60 executes an operating system and an application for generating training data. The functionality of the application for generating training data is described below in greater detail. The RAM 64 provides relatively responsive volatile storage to the CPU 60. The I/O interface 68 enables an administrator to interact with the system 20 via a keyboard, a mouse, a speaker, and a display. The network interface 72 permits wired or wireless communication with other systems, such as the client computing devices. The non-volatile storage 76 stores computer readable instructions for implementing the operating system and the application for generating training data, as well as a biological sequence database 84 and any data used by the application. The application generates training data from original biological sequences for use in supervised and unsupervised learning from biological sequences. During operation of the system 20, the computer readable instructions for the operating system, and the application, and the data may be retrieved from the non-volatile storage 76 and placed in the RAM 64 to facilitate execution.

Figure 2:
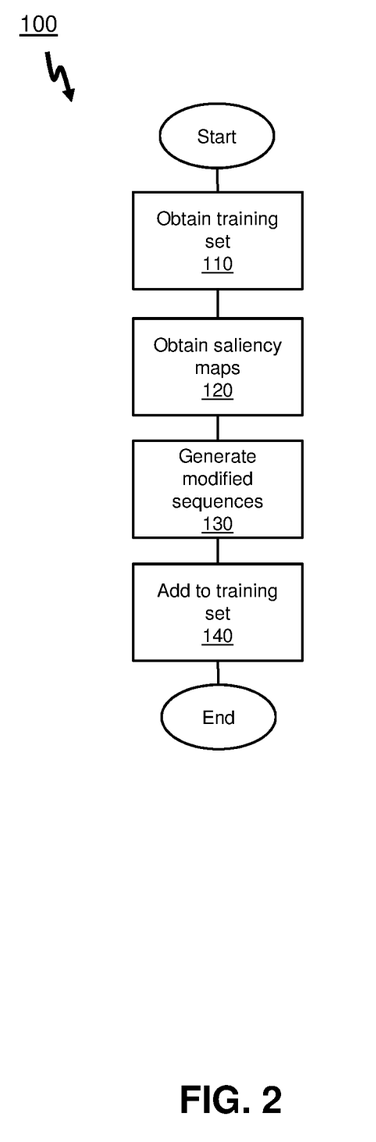
FIG. 2 is a flow chart of the general method for generating biological sequences for training machine learning models used by the system of FIG. 1.

The general method 100 of generating training data for use in supervised and unsupervised learning from biological sequences using the system 20 will now be described with reference to FIGS. 1 and 2. The method 100 commences with the obtaining of a training set for a machine learning model (110). The training set includes one or more original biological sequences retrieved from the biological sequence database 84. Next, saliency maps for one or more of the one or more original biological sequences are obtained (120). Then, for one or more elements in the one or more original biological sequences, the corresponding saliency map values are used to generate a modified element in one or more modified biological sequences (130). Upon generating the modified biological sequences, they are added to the training set to form an expanded training set (140). The modified biological sequences are placed in the biological sequence database 84 to supplement the original biological sequences.

Figure 3:
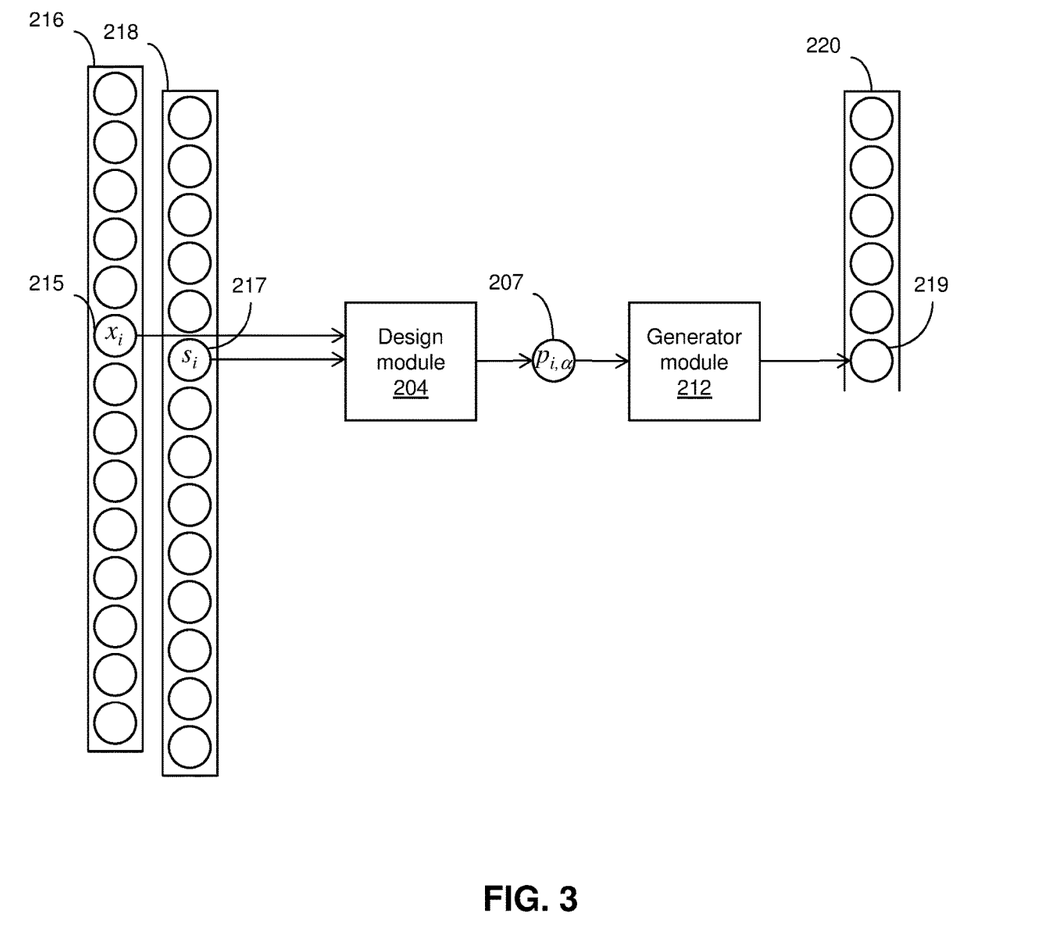
FIG. 3 shows the use of a design module and a generator module in the generation of biological sequences for training machine learning models using the system of FIG. 1.

FIG. 3 illustrates two modules of the application executed by the system 20. A design module 204 uses an element 215 in an original biological sequence 216 and an element 217 in a saliency map 218 to determine a set of generator parameters 207. The generator parameters correspond to probabilities of possible modified sequence elements. A generator module 212 uses the set of generator parameters 207 to produce an element 219 in a modified biological sequence 220.

Figure 4:
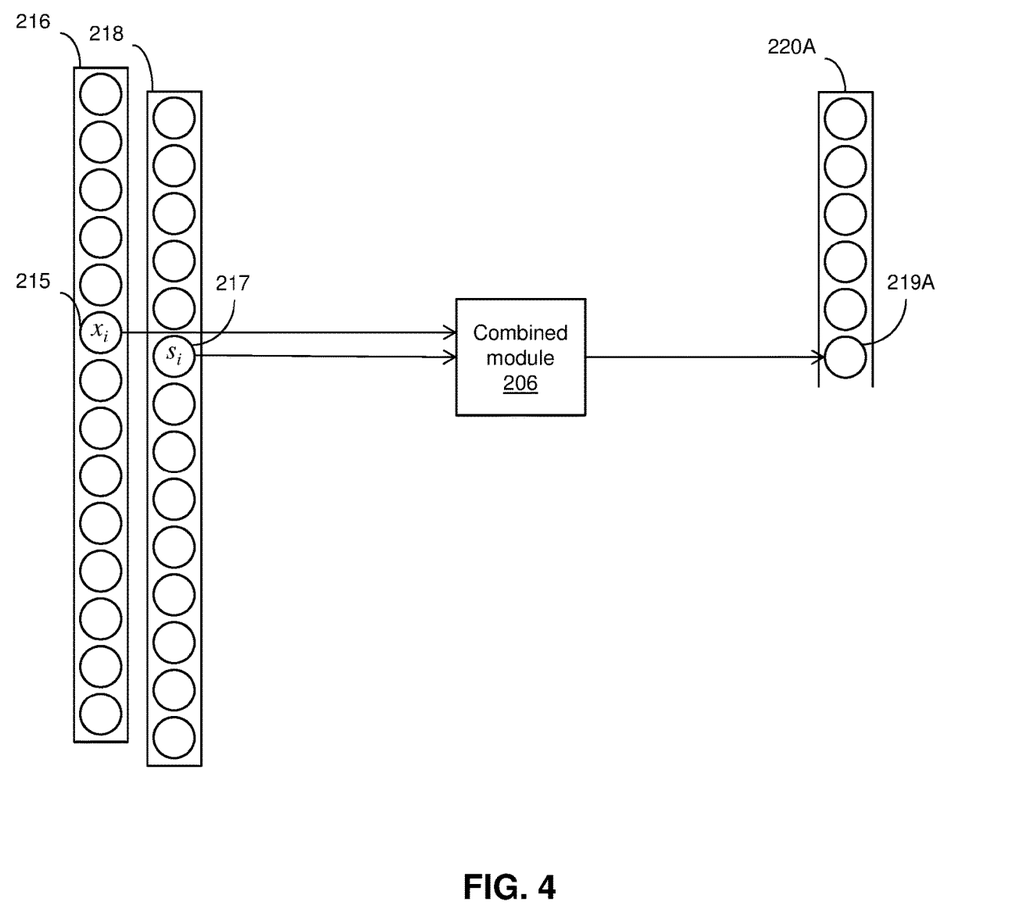
FIG. 4 shows the use of a combined module in the generation of biological sequences.

FIG. 4 illustrates the use of a combined module 206 in another embodiment wherein the functionality of the design module and the generator module are combined into the single combined module 206. The combined module 206 uses the element 215 in the original biological sequence 216 and the element 217 in the saliency map 218 to produce an element 219A in a modified biological sequence 220A.

Figure 5:
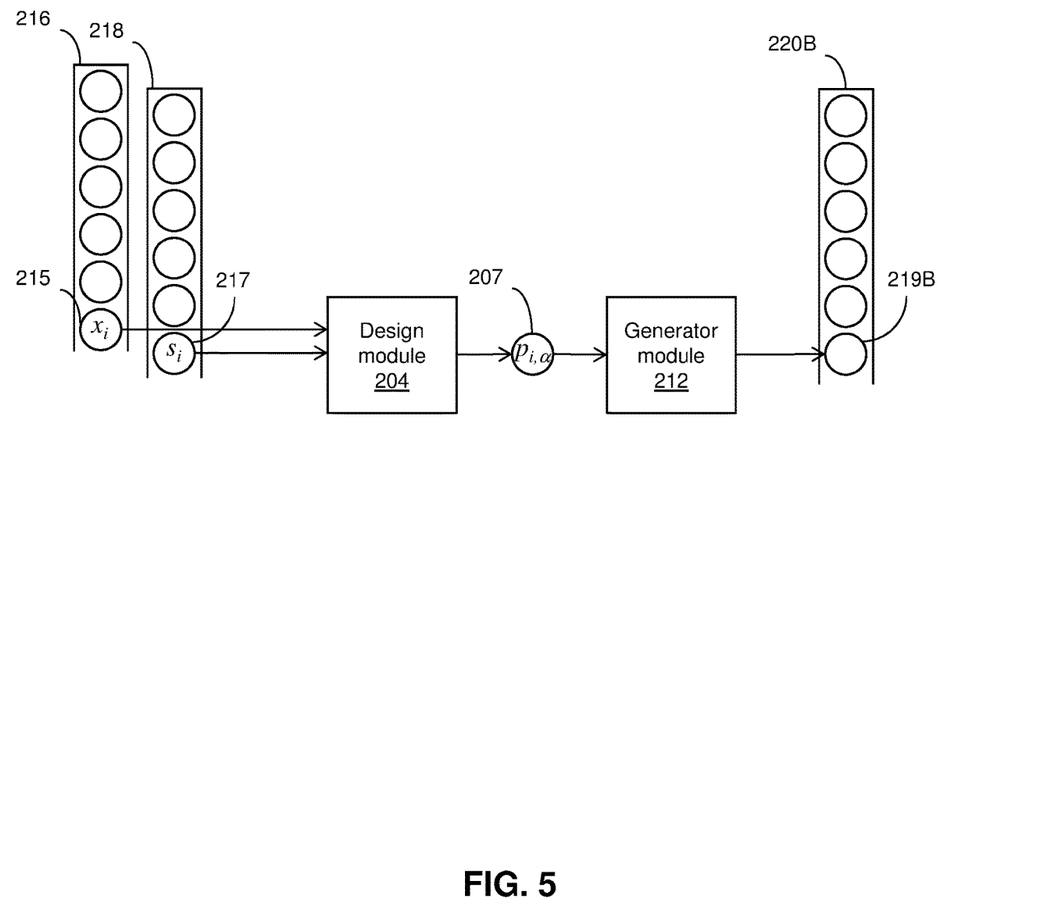
FIG. 5 shows that the original sequence and the saliency map may be processed sequentially.

FIG. 5 illustrates that the original sequence and the saliency map may be processed sequentially, that is, element by element, to generate an element 219B in a modified biological sequence 220B, and need not be entirely stored in memory.

Figure 6:
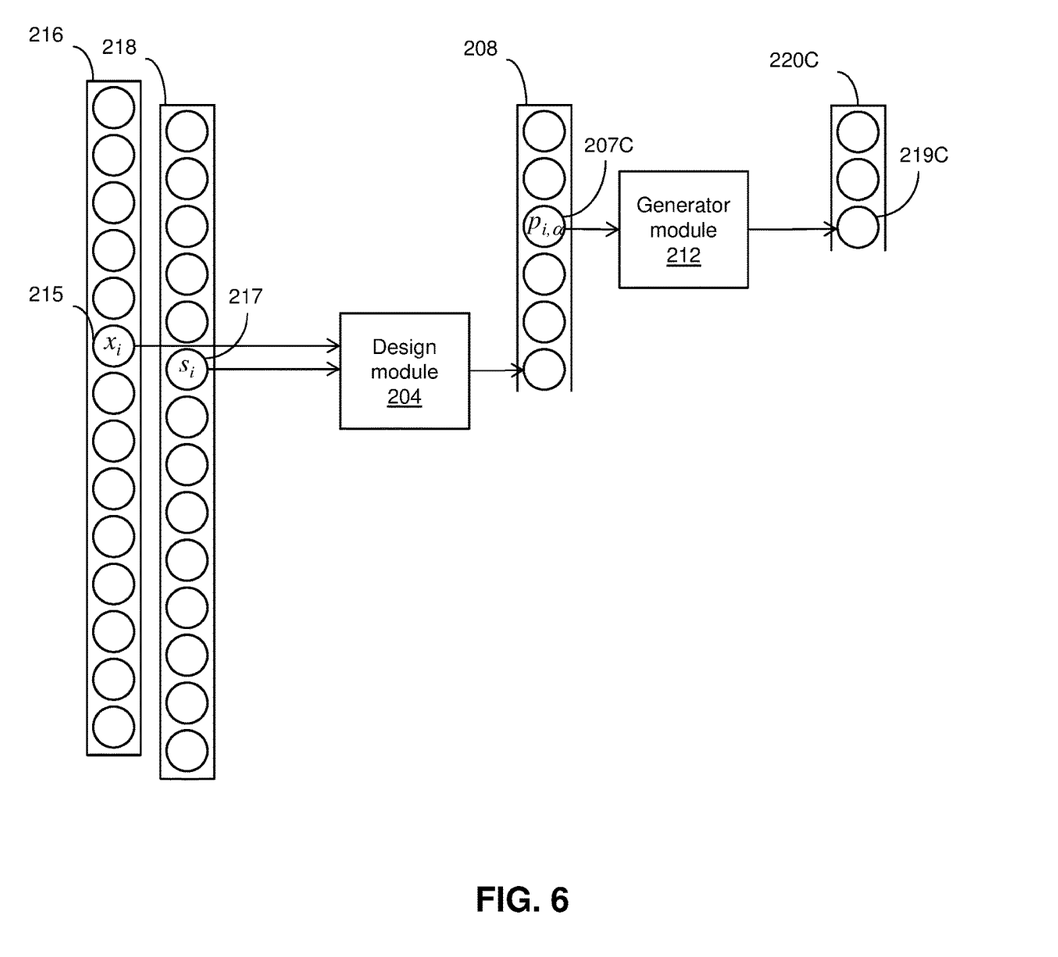
FIG. 6 shows that the design module and the generator module may operate in a pipeline fashion.

FIG. 6 illustrates that the design module 204 and the generator module 212 may operate in a pipeline fashion in another embodiment, wherein the design module 204 produces a sequence of generator parameters 208 and the generator module 212 uses a set of generator parameters 207C in the sequence of generator parameters 208 to produce an element 219C in a modified biological sequence 220C.

Figure 7:
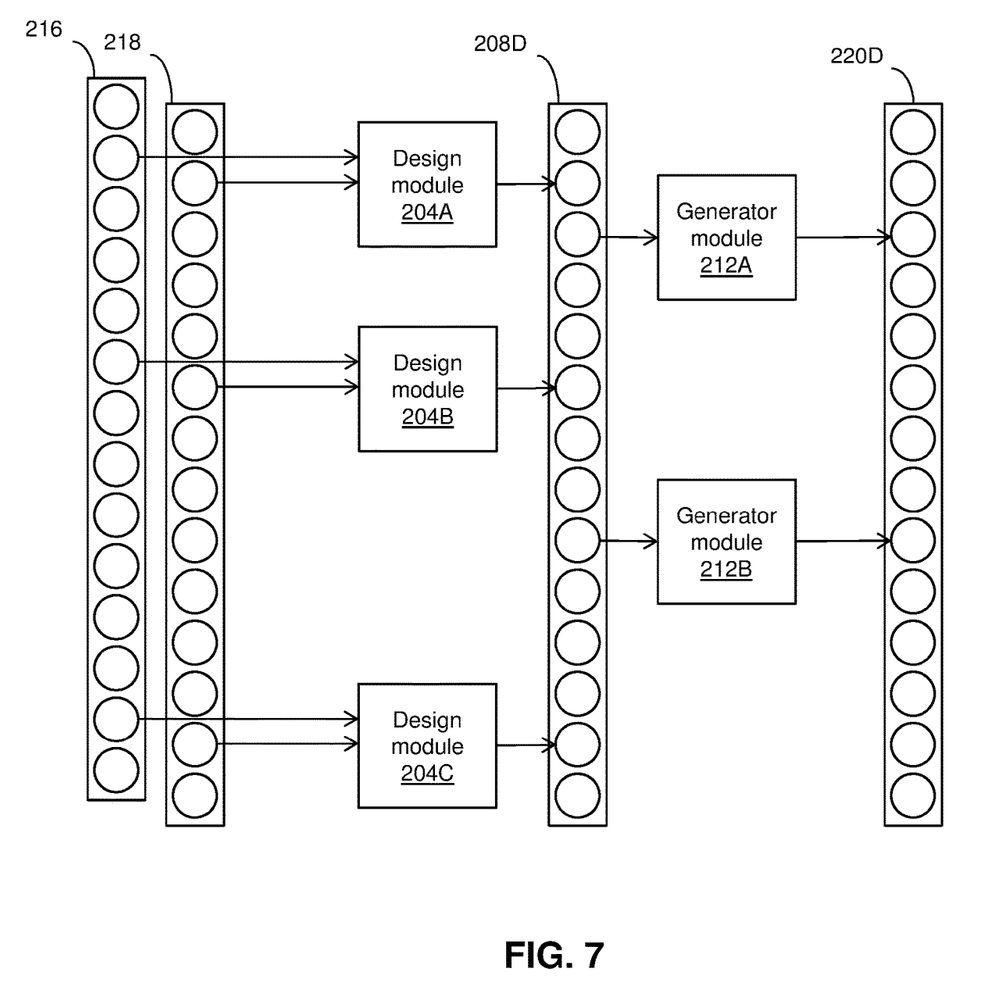
FIG. 7 shows that multiple processors can be used.

FIG. 7 illustrates that multiple processors can be used in a further embodiment so that multiple design modules 204A, 204B and 204C operate concurrently to produce a sequence of generator parameters 208D, and that multiple generator modules 212A, 212B operate concurrently to produce elements in a modified sequence 220D. It will be appreciated that different numbers of design modules may be used and that different numbers of generator modules may be used.

Figure 8:
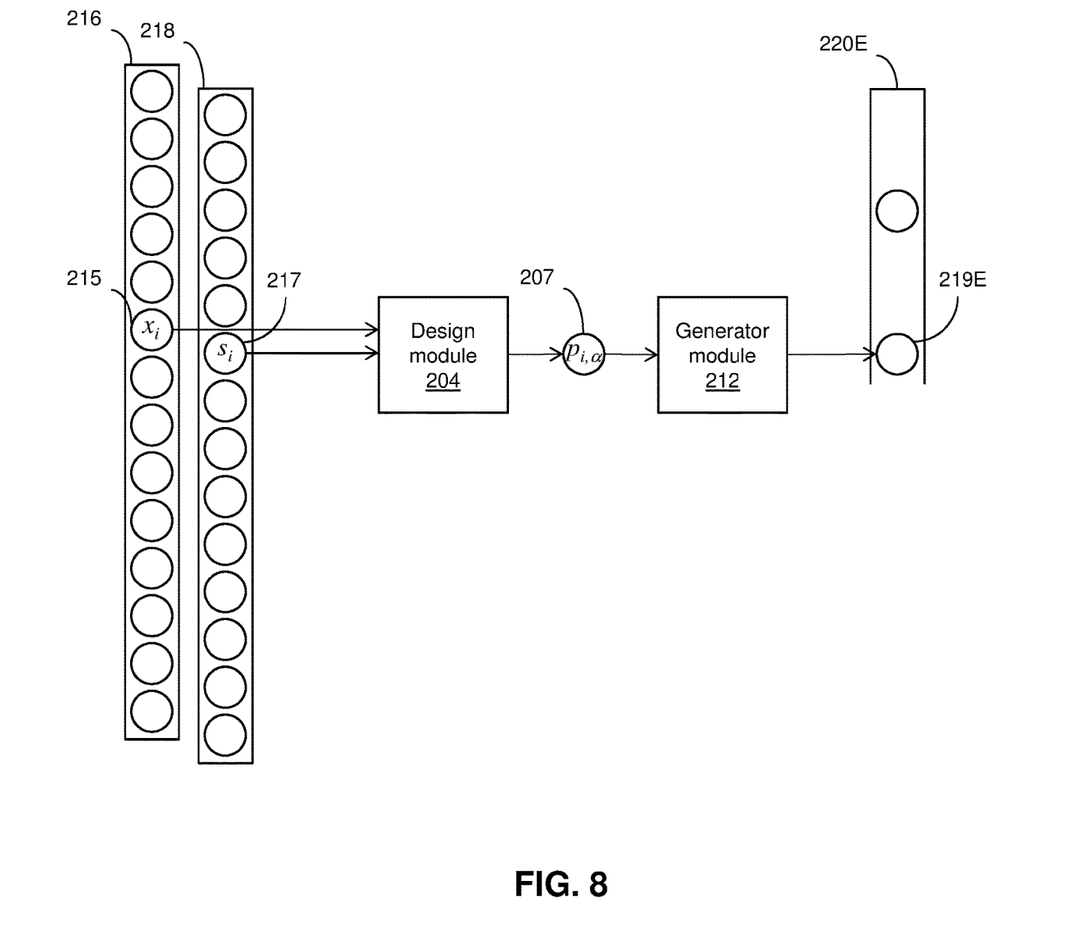
FIG. 8 shows that only a subset of elements in the modified biological sequence may be generated.

FIG. 8 illustrates that only a subset of elements 219E in a modified biological sequence 220E may be generated in some scenarios.

Figure 9:
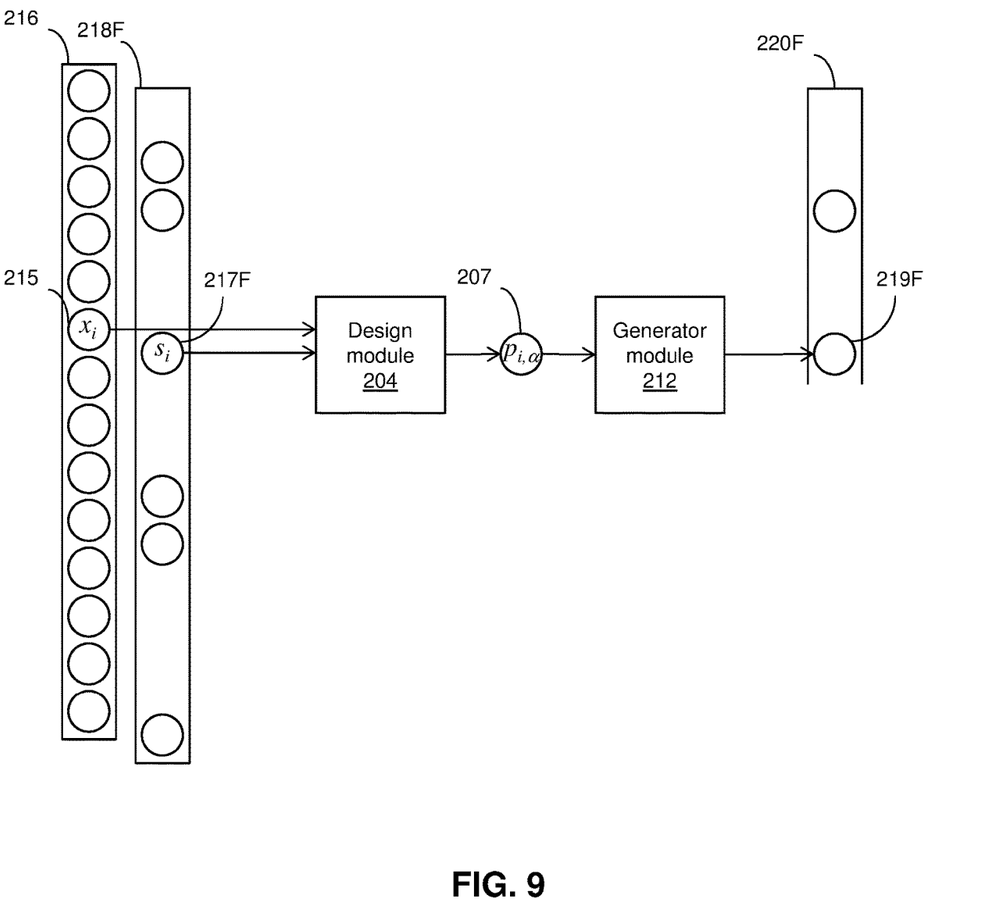
FIG. 9 shows that only a subset of the elements in the saliency map may be provided and that only a subset of the corresponding elements in the modified biological sequence may be generated.

FIG. 9 illustrates that only a subset of elements 217F in a saliency map 218F may be provided and that only a subset of corresponding elements 219F in a modified biological sequence 220F may be generated.

It will be appreciated that the aspects illustrated in FIGS. 4 to 9 can be combined in various ways in different embodiments.

The systems and methods described herein take one or more original biological sequences as input and generate one or more modified biological sequences. Symbols and notations to represent the elements and operations performed by the different modules are described herein. It will be appreciated that different symbols and notations may describe the same embodiment. It will be appreciated that different embodiments may be produced by standard rearrangements of operations. For instance, a plus b plus c can be determined by adding a to b and then adding c, by adding b to a and then adding c, by adding b to c and then adding a, and so on.

The notation "a←b" indicates that the output produced by an operation b is stored in a memory location associated with the symbol a.

Denote a DNA, an RNA or a protein sequence of length n by $x_1, x_2, \ldots, x_n$, where the alphabet of element $x_i$ is $A_i$, that is $x_i \in A_i$. The number of elements in $A_i$, its cardinality, is denoted $k_i$. For DNA, $A_i = \{A, C, G, T\}$ and $k_i = 4$; for RNA, $A_i = \{A, C, G, U\}$ and $k_i = 4$; and for protein sequences, $A_i = \{A, C, D, E, F, G, H, I, K, L, M, N, P, Q, R, S, T, V, W, Y\}$ and $k_i = 20$. The elements may have been taken consecutively from a biological sequence. The elements may have been taken nonconsecutively from a biological sequence. The elements may be taken from multiple biological sequences.

An original sequence $x_1, x_2, \ldots, x_n$ is used to generate a modified sequence $\hat{x}_1, \hat{x}_2, \ldots, \hat{x}_n$ that has the same length, or is used to generate a modified sequence $\hat{x}_1, \hat{x}_2, \ldots, \hat{x}_m$ that has a different length, where $m \neq n$. The alphabet of $\hat{x}_i$ is denoted $\hat{A}_i$ and the number of elements in $\hat{A}_i$, its cardinality, is denoted $\hat{k}_i$. In one embodiment, the alphabet of $\hat{x}_i$ is the same as the alphabet of $x_i$, that is, $\hat{A}_i = A_i$ and $\hat{k}_i = k_i$. In another embodiment, only some of the elements in the original biological sequence are used to generate elements in the modified biological sequence, which will produce a modified biological sequence that is shorter than the original biological sequence. In another embodiment, the alphabet of $\hat{x}_i$ is extended to include the null symbol Ø, which accounts for deletions of the element in the modified sequence, so that $\hat{k}_i = k_i + 1$. It will be appreciated that a modified sequence that includes null symbols can be used to produce a shorter modified sequence without null symbols by removing the corresponding elements.

Figure 10A:
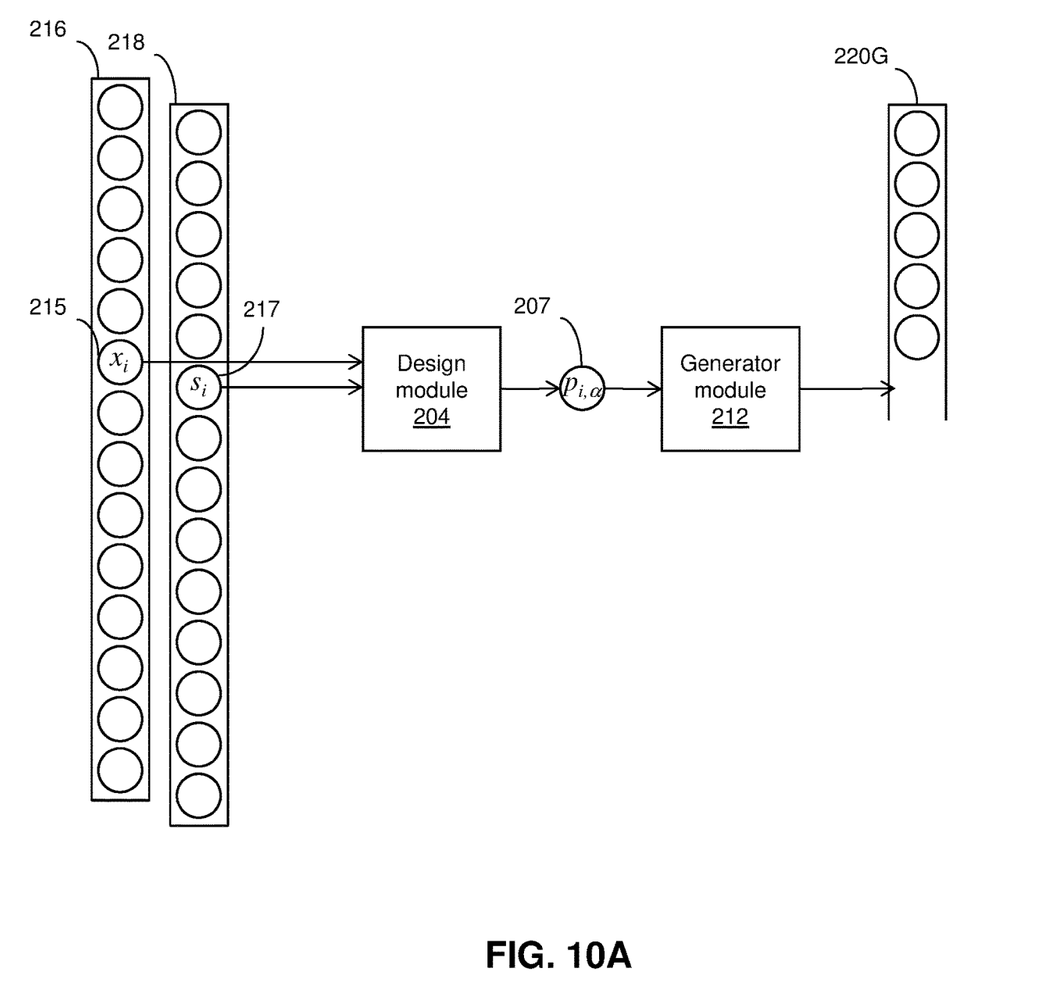
FIG. 10A and FIG. 10B show the generation of a biological sequence, by the system of FIG. 1, with a deleted element.
Figure 10B:
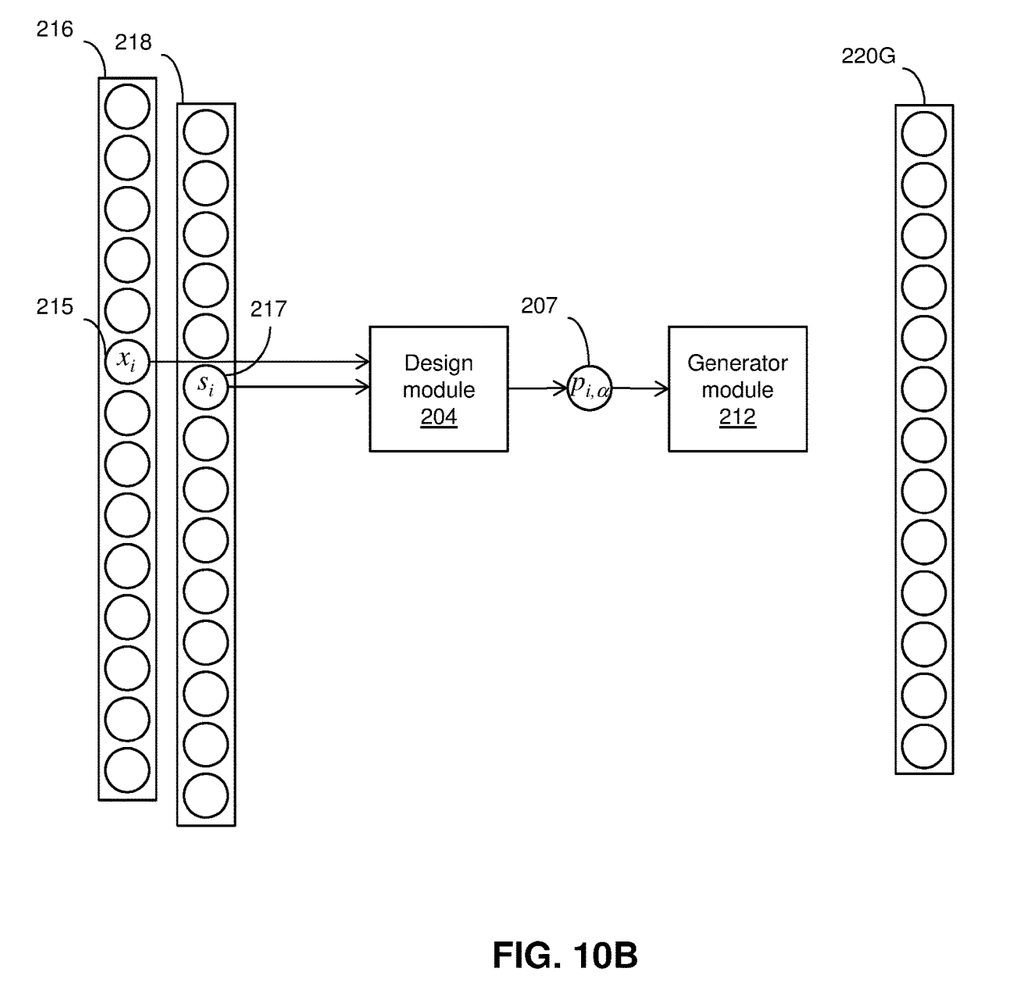

In another embodiment as illustrated in FIG. 10A, the null symbol is not inserted into a modified sequence 220G generated from an original sequence 216, and the modified sequence may be generated without a replacement for the element of the original sequence. FIG. 10B shows the final modified sequence 220G upon completion of the generation. As shown, the modified sequence is one element shorter than the original sequence.

Saliency maps are used to guide the generation of modified sequences. For each original sequence, the system may use a saliency map, which for each element provides information pertaining to the invariance of biological function to that element. Elements with high saliency are more likely to be pertinent to biological function than elements with low saliency. For element $x_i$, denote the saliency by $s_i$. For an original sequence $x_1, x_2, \ldots, x_n$, the salience map is $s_1, s_2, \ldots, s_n$. If a subset of the elements in the original sequence are to be modified, the saliency map may be provided for that subset.

The saliency map directs the process of generating a new sequence and it may be obtained from various sources, including evolutionary conservation, derived allele frequency, DNA accessibility, ChIP-Seq data, CLIP-Seq data, SELEX data, massively parallel reporter assays and mutational studies using, for example, CRISPR/Cas9. The saliency map may be derived by aligning an original biological sequence to other related sequences, such as from different species or from different patients, or it may be derived by aligning an original biological sequence to the reference genome and then examining information that has been previously associated with the reference genome and stored. In the case of labeled biological sequences, the saliency map may be determined differently depending on the label of the sequence. For instance, if the goal is to train a system to predict whether a specific protein will bind to an RNA sequence, then we may determine the saliency maps of sequences that are known to bind to the protein differently than than those that are known to not bind to the protein.

It is assumed that $s_i$ is between zero and one and it will be appreciated that if the values provided are outside of this range, they may be normalized to be in this range. Furthermore, nonlinear transformations may be applied to the provided values to obtain the values forming the saliency map. For instance, the level of conservation of a particular nucleotide across mammals may be normalized to be between zero and one, where zero indicates low conservation (low saliency) and one indicates high conservation (high saliency). It will be appreciated that a different range for $s_i$ may be used and the embodiments described below may be modified to account for the different range.

A saliency map may be obtained by combining multiple base saliency maps. For example, a saliency map may be produced from a weighted average of two or more base saliency maps. Other combinations will occur to those skilled in the art. For instance, if the base saliency $s_i^m$ is the conservation across a variety of different mammals and the base saliency $s_i^h$ is the conservation across a human population, we may set $s_i \leftarrow 1-(1-s_i^m)(1-s_i^h)$ so that the saliency is low if the base saliency is low in both humans and mammals, and the saliency is high if the base saliency is high in either humans or mammals. In another particular embodiment, nearby saliency values in a single base saliency map may be combined to produce a smoother saliency map: If the base saliency map is $s_1^b, s_2^b, \ldots, s_2^b$, we may set $s_i \leftarrow \sum_{j=-w}^{j=w} \theta_j s_{i+j}^b$ for $w+1 \leq i \leq n-w$, where w is the half-width of the smoothing window (a positive integer), and $\theta_{-w}, \theta_{-w+1}, \ldots, \theta_{w-1}, \theta_w$ is a set of smoothing weights with the property that $\sum_{j=-w}^{j=w} \theta_j = 1$.

To generate an element in a modified sequence, a design module is used to determine a set of generator parameters. The design module may be applied to all elements in the original sequences and the generator parameters may be stored for later use in generating modified sequences. The design module may be applied as needed, that is, when a specific modified sequence is to be generated or when a specific element within a modified sequence is to be generated, the design module may be applied to obtain the needed generator parameters. Once generator parameters have been determined by the design module, they may be stored for re-use, or they may be discarded, in which case if the same element in an original sequence is to be modified, the design module will need to be re-applied. The design module and the generator module may operate in a pipeline fashion, such that the design module is computing generator parameters for generator modules that will soon be applied and at the same time generator modules are being applied using previously determined generator parameters. The design module and the generator module may be implemented as a single module. Design modules and generator modules may be operated in parallel using a plurality of computing units or hardware units, which may include CPUs, GPUs and FPGAs. It will be appreciated that there are several ways of combining the operations of the design modules and the generator modules to achieve the same effect.

In one embodiment, the design module takes as input an original element $x_i$ and its corresponding saliency $s_i$ and outputs a set of generator parameters corresponding to the probabilities of different values in $\hat{A}_i$ that $\hat{x}_i$ can take on. The generator parameters, that is, the output of the design module, for original element $x_i$ are denoted $p_{i,\alpha}$ for $\alpha \in \hat{A}_i$. The design module operates as follows:

$$p_{i,\alpha} \leftarrow d_\alpha(x_i, s_i), \text{for all } \alpha \in \hat{A}_i,$$

where $p_{i,\alpha} \geq 0$, $\forall \alpha \in \hat{A}_i$ and $\Sigma_{\alpha \in \hat{A}_i} p_{i,\alpha} = 1$. The symbol "←" indicates that the output of the operation indicated to its right is stored in a memory location associated with the symbol to its left, that is, for every value $\alpha \in \hat{A}_i$, the output of the design module $d_\alpha(x_i, s_i)$ is stored in the memory associated with $p_{i,\alpha}$.

Broadly, the design module has the property that if the saliency is increased, the original element is more likely to be preserved. So, the design module has the property that if $s_i' > s_i$ then $d_\alpha(\alpha, s_i') > d_\alpha(\alpha, s_i)$ for all $\alpha \in \hat{A}_i$. Any design module that has this property may be used.

In one embodiment, the design module outputs generator parameters that can be interpreted as probabilities and wherein the value of the original element is copied to the modified element with probability $s_i$ and otherwise the modified element is chosen uniformly from across all possible values of $\hat{x}_i$. This design module operates as follows:

$$d_\alpha(x_i, s_i) = s_i I(\alpha, x_i) + (1-s_i)/\hat{k}_i$$

where $\hat{k}_i$ is the number of values that $\hat{x}_i$ can take on, and $I(\cdot)$ is the indicator operator which outputs 1 if $\alpha = x_i$ and outputs 0 otherwise. It will be appreciated that there are different ways in which the design module may be constructed so as to achieve the same effect. For instance, the generator parameters may be directly set as follows: First, for all $\alpha \in \hat{A}_i$ set $p_{i,\alpha} \leftarrow (1-s_i)/\hat{k}_i$, and then set $p_{i,x_i} \leftarrow p_{i,x_i} + s_i$.

It will be appreciated that the above is a special case of the following more general form:

$$d_\alpha(x_i, s_i) = h(s_i) I(\alpha, x_i) + (1-h(s_i))/\hat{k}_i$$

wherein h( ) is a transformation in which $h(s_i) = s_i$. In other embodiments, the design module 204 applies a linear or nonlinear transformation $h(s_i)$ to the saliency, so as to more or less strongly preserve elements. Values of $h(s_i)$ fall between zero and one. In one particular embodiment, the transformation may satisfy $h(s_i) = s_i - 1/\hat{k}_i$, in which case the value of the original element is copied to the modified element with probability $s_i$ and otherwise the modified element is chosen uniformly at random from the remaining $\hat{k}_i-1$ possible values. In another particular embodiment, the transformation may satisfy $h(s_i)=(s_i)^r$, where r is a predetermined parameter satisfying r>0. For r<1 the transformation increases $s_i$ so that salient elements are more strongly preserved, whereas for r>1 the transformation decreases $s_i$ so that salient elements are less strongly preserved. It will be appreciated that different transformations may be used, although they are required to have outputs between zero and one.

In another embodiment, the design module is configured so that instead of using a uniform distribution with probability $1-h(s_i)$, a non-uniform distribution is used. This distribution may reflect the frequencies of nucleotides from across the genome or from related genomic sequences. Or, the frequencies of amino acids from across the proteome or from related protein sequences may be used. It will be appreciated that other forms of distributions may be used for the design module. To account for this, the saliency map can be extended to include, for each element $x_i$, a non-uniform distribution $s_{i,\alpha}'$, $\alpha \in \hat{A}_i$ satisfying $s_{i,\alpha}' \geq 0$, $\forall \alpha \in \hat{A}_i$ and $\Sigma_{\alpha e \in A_i} s_{i,\alpha}'=1$. In one embodiment, the design module operates as follows:

$$d_\alpha(x_i,s_i)=h(s_i)I(\alpha,x_i)+(1-h(s_i))s_{i,\alpha}'$$

For instance, $s_{i,\alpha}'$ could be the frequency of allele $\alpha$ across a human population, so that alleles with higher frequency receive higher generator parameter values.

In another embodiment, the original element is preserved with probability $h(s_i)$ and otherwise an element is generated that must be different from the original element. This can be achieved by using a design module that operates as follows:

$$d_\alpha(x_i,s_i)=h(s_i)I(\alpha,x_i)+(1-h(s_i))(1-I(\alpha,x_i))s_{i,\alpha}'$$

where in this embodiment $s_{i,\alpha}'$ has the property $\Sigma_{\alpha \in \hat{A}_i, \alpha \neq x_i} s_{i,\alpha}'=1$.

The generator module uses the generator parameters $p_{i,\alpha}$, $\alpha \in \hat{A}_i$ that are determined by the design module for the original element $x_i$, and outputs an element $\hat{x}_i$ in the modified biological sequence. In one embodiment, a pseudorandom number generator is used to sample a value from the probability distribution $p_{i,\alpha}$, $\alpha \in \hat{A}_i$. This may be performed by dividing the interval from zero to one using the probabilities $p_{i,\alpha}$, $\alpha \in \hat{A}_i$ and then identifying the corresponding value $\hat{x}_i$ using a pseudorandom number between zero and one. In another embodiment, a data file which may be stored in volatile or non-volatile memory is used to set the value of $\hat{x}_i$ by comparing values in the data file with the parameters $p_{i,\alpha}$, $\alpha \in \hat{A}_i$. In another embodiment, a computer module that outputs a sequence of numbers is used to set the value of $\hat{x}_i$ by comparing values in the sequence of numbers with the parameters $p_{i,\alpha}$, $\alpha \in \hat{A}_i$. In another embodiment, an electrical voltage or an electrical current that is derived from a physical sensor such as a heat, light or motion sensor is converted to a digital value and the digital value is compared to the parameters $p_{i,\alpha}$, $\alpha \in \hat{A}_i$ to determine the value of $\hat{x}_i$.

In one embodiment, the generator module is configured so that if it is repeatedly applied, the relative frequency with which $\hat{x}_i=\alpha$ will converge to $p_{i,\alpha}$. It will be appreciated that there are several ways of achieving this, including using a pseudorandom number generator to sample a value from the probability distribution $p_{i,\alpha}$, $\alpha \in \hat{A}_i$. It will be appreciated that it may be sufficient for the generator module to have the property that if it is repeatedly applied, the relative frequency with which $\hat{x}_i=\alpha$ will converge to a value that is within $\in$ of $p_{i,\alpha}$, where $\in$ is less than one half of the minimum absolute difference between all pairs of generator parameters.

In another embodiment, the generator parameters for multiple elements in the original sequence are determined using the design module and they are combined to produce the elements in the modified sequence. For instance, the saliency values may be sorted and the elements in the original sequence that are among the top 50% in saliency values may be copied directly to the modified sequence, whereas for the bottom 50%, the elements in the modified sequence may be generated uniformly from the alphabet.

The system and method described herein can be applied to generate additional training cases for a selected subset of the original sequences, which may be identified as "problematic cases" based on validation performance or using additional data.

Although the invention has been described with reference to certain specific embodiments, various modifications thereof will be apparent to those skilled in the art without departing from the spirit and scope of the invention as outlined in the claims appended hereto.

The invention claimed is:

1. A computer-implemented method for training a supervised machine learning model with an expanded training set using biological sequences, comprising:
   obtaining a set of original biological sequences comprising deoxyribonucleic acid (DNA) sequences, ribonucleic acid (RNA) sequences, or protein sequences;
   obtaining saliency values corresponding to one or more elements in each of the set of original biological sequences, wherein a saliency value of the saliency values corresponding to an element of the one or more elements indicates a degree of pertinence of the element to biological function, wherein the saliency values are derived from one or more of: evolutionary conservation across at least two different species, allele frequency in a human population of at least two humans, DNA accessibility, chromatin immunoprecipitation sequencing (ChIP-Seq), cross-linking immunoprecipitation sequencing (CLIP-Seq), systematic evolution of ligands by exponential enrichment (SELEX), a massively parallel reporter assay, and a mutational study;
   applying one or more modifications to each of the set of original biological sequences to create a set of modified biological sequences, and associating each of the set of modified biological sequences with an original biological sequence, wherein each of the set of original biological sequences has an associated label, and wherein each of the set of modified biological sequences is associated with the same label as the associated original biological sequence;
   generating one or more elements in each of the set of modified biological sequences using one or more elements in the associated original biological sequence and the corresponding saliency values, wherein a probability that an element in each of the set of modified biological sequences is the same as the elements in the associated original biological sequence is higher for larger corresponding saliency values, and wherein a biological function of the set of modified biological sequences is maintained relative to the associated original biological sequence;
   creating an expanded training set comprising the obtained set of original biological sequences and the set of modified biological sequences; and training the supervised machine learning model using the expanded training set.

2. The computer-implemented method of claim 1, wherein the supervised machine learning model comprises one or more of: a mixture model, a hidden Markov model, an autoencoder, a recurrent neural network, linear regression, a neural network, a random forest, and a support vector machine.

3. The computer-implemented method of claim 1, wherein generating the one or more elements in each of the set of modified biological sequences using the one or more elements in the associated original biological sequence and the corresponding saliency values further comprises:
   determining a set of generator parameters from the one or more elements in the associated original biological sequence and the corresponding saliency values, wherein the set of generator parameters corresponds to probabilities of different values in a set $\hat{A}_i$ of possible values that a modified element $\hat{x}_i$ of the one or more elements in the associated original biological sequence can take on; and
   using the set of generator parameters to generate at least one of the one or more elements in each of the set of modified biological sequences.

4. The computer-implemented method of claim 1, wherein generating the one or more elements in each of the set of modified biological sequences further comprises producing a null symbol, wherein the null symbol represents a deleted element in at least one of the set of modified biological sequences.

5. The computer-implemented method of claim 1, wherein a probability of generating a value $\alpha$ for an element $\hat{x}_i$ in the one or more elements in each of the one or more modified biological sequences is expressed by:

$$h(s_i)I(\alpha, x_i)+(1-h(s_i))/\hat{k}_i$$

wherein $x_i$ denotes an element in the original biological sequence, $s_i$ denotes a saliency value, $\hat{k}_i$ denotes a number of possible values for $\hat{x}_i$, $I(\cdot)$ denotes an indicator operator which outputs 1 if $\alpha=x_i$ and outputs 0 otherwise, and $h(s_i)$ denotes a linear or non-linear transformation of $s_i$.

6. The computer-implemented method of claim 1, wherein a probability of generating a value $\alpha$ for an element $\hat{x}_i$ in the one or more elements in each of the one or more modified biological sequences is expressed by:

$$h(s_i)I(\alpha, x_i)+(1-h(s_i))s_{i,\alpha}'$$

wherein $x_i$ denotes an element in the original biological sequence, $s_i$ denotes a saliency value, $I(\cdot)$ denotes an indicator operator which outputs 1 if $\alpha=x_i$ and outputs 0 otherwise, $h(s_i)$ denotes a linear or non-linear transformation of $s_i$, and $s_{i,\alpha}'$ denotes a non-uniform distribution over $\alpha \in \hat{A}_i$ satisfying $s_{i,\alpha}' \geq 0$, $\forall \alpha \in \hat{A}_i$ and $\Sigma_{\alpha \in \hat{A}_i} s_{i,\alpha}'=1$, wherein $\hat{A}_i$ denotes a set of possible values for $\hat{x}_i$.

7. The computer-implemented method of claim 6, wherein the non-uniform distribution corresponds to frequencies of nucleotides from across a genome of the original biological sequence.

8. The computer-implemented method of claim 1, wherein the saliency values are derived from one or more of: evolutionary conservation across at least two different species, and allele frequency in a human population of at least two humans.

9. The computer-implemented method of claim 1, wherein the supervised machine learning model is trained for determining a molecular phenotype of a biological sequence, and wherein each of the set of original biological sequences has an associated label of a molecular phenotype.

10. A computer-implemented system for training a supervised machine learning model with an expanded training set using biological sequences, comprising one or more computer processors and one or more storage devices having instructions stored thereon that, when executed by the one or more computer processors, cause the one or more computer processors to perform operations comprising:
   obtaining a set of original biological sequences comprising deoxyribonucleic acid (DNA) sequences, ribonucleic acid (RNA) sequences, or protein sequences;
   obtaining saliency values corresponding to one or more elements in each of the set of original biological sequences, wherein a saliency value in the saliency values corresponding to an element of the one or more elements indicates a degree of pertinence of the element to biological function, wherein the saliency values are derived from one or more of: evolutionary conservation across at least two different species, allele frequency in a human population of at least two humans, DNA accessibility, chromatin immunoprecipitation sequencing (ChIP-Seq), cross-linking immunoprecipitation sequencing (CLIP-Seq), systematic evolution of ligands by exponential enrichment (SELEX), a massively parallel reporter assay, and a mutational study;
   applying one or more modifications to each of the set of original biological sequences to create a set of modified biological sequences, and associating each of the set of modified biological sequences with an original biological sequence, wherein each of the set of original biological sequences has an associated label, and wherein each of the set of modified biological sequences is associated with the same label as the associated original biological sequence;
   generating one or more elements in each of the set of modified biological sequences using one or more elements in the associated original biological sequence and the corresponding saliency values, wherein a probability that an element in each of the set of modified biological sequences is the same as the elements in the associated original biological sequence is higher for larger corresponding saliency values, and wherein a biological function of the set of modified biological sequences is maintained relative to the associated original biological sequence;
   creating an expanded training set comprising the obtained set of original biological sequences and the set of modified biological sequences; and
   training the supervised machine learning model using the expanded training set.

11. The computer-implemented system of claim 10, wherein the supervised machine learning model comprises one or more of: a mixture model, a hidden Markov model, an autoencoder, a recurrent neural network, linear regression, a neural network, a random forest, and a support vector machine.

12. The computer-implemented system of claim 10, wherein generating the one or more elements in each of the set of modified biological sequences using the one or more elements in the associated original biological sequence and the corresponding saliency values further comprises:
   determining a set of generator parameters from the one or more elements in the associated original biological sequence and the corresponding saliency values, wherein the set of generator parameters corresponds to probabilities of different values in a set $\hat{A}_i$ of possible values that a modified element $\hat{x}_i$ of the one or more elements in the associated original biological sequence can take on; and using the set of generator parameters to generate at least one of the one or more elements in each of the set of modified biological sequences.

13. The computer-implemented system of claim 10, wherein generating the one or more elements in each of the set of modified biological sequences further comprises producing a null symbol, wherein the null symbol represents a deleted element in at least one of the set of modified biological sequences.

14. The computer-implemented system of claim 10, wherein a probability of generating a value $\alpha$ for an element $\hat{x}_i$ in the one or more elements in each of the one or more modified biological sequences is expressed by:

$$h(s_i)I(\alpha,x_i)+(1-h(s_i))/\hat{k}_i$$

wherein $x_i$ denotes an element in the original biological sequence, $s_i$ denotes a saliency value, $\hat{k}_i$ denotes a number of possible values for $\hat{x}_i$, $I(\cdot)$ denotes an indicator operator which outputs 1 if $\alpha=x_i$ and outputs 0 otherwise, and $h(s_i)$ denotes a linear or non-linear transformation of $s_i$.

15. The computer-implemented system of claim 10, wherein a probability of generating a value $\alpha$ for an element $\hat{x}_i$ in the one or more elements in each of the one or more modified biological sequences is expressed by:

$$h(s_i)I(\alpha,x_i)+(1-h(s_i))s_{i,\alpha}'$$

wherein $x_i$ denotes an element in the original biological sequence, $s_i$ denotes a saliency value, $I(\cdot)$ denotes an indicator operator which outputs 1 if $\alpha=x_i$ and outputs 0 otherwise, $h(s_i)$ denotes a linear or non-linear transformation of $s_i$, and $s_{i,\alpha}'$ denotes a non-uniform distribution over $\alpha \in \hat{A}_i$ satisfying $s_{i,\alpha}' \geq 0$, $\forall \alpha \in \hat{A}_i$ and $\Sigma_{\alpha \in \hat{A}_i} s_{i,\alpha}' = 1$, wherein $\hat{A}_i$ denotes a set of possible values for $\hat{x}_i$.

16. The computer-implemented system of claim 15, wherein the non-uniform distribution corresponds to frequencies of nucleotides from across a genome of the original biological sequence.

17. The computer-implemented system of claim 10, wherein the saliency values are derived from one or more of: evolutionary conservation across at least two different species, and allele frequency in a human population of at least two humans.

18. The computer-implemented system of claim 10, wherein the supervised machine learning model is trained for determining a molecular phenotype of a biological sequence, and wherein each of the set of original biological sequences has an associated label of a molecular phenotype.

* * * * *